United States Patent
Ferraro et al.

(10) Patent No.: US 11,709,195 B2
(45) Date of Patent: Jul. 25, 2023

(54) SYSTEM FOR MONITORING FOR PARTIAL DISCHARGES IN AN ITEM OF ELECTRICAL EQUIPMENT VIA GASEOUS EMISSIONS

(71) Applicant: Schneider Electric Industries SAS, Rueil Malmaison (FR)

(72) Inventors: Venanzio Ferraro, Grenoble (FR); Diego Alberto, Corenc (FR); Maxime Durand, Grenoble (FR)

(73) Assignee: Schneider Electric Industries SAS, Rueil Malmaison (FR)

( * ) Notice: Subject to any disclaimer, the term of this patent is extended or adjusted under 35 U.S.C. 154(b) by 359 days.

(21) Appl. No.: 16/989,536

(22) Filed: Aug. 10, 2020

(65) Prior Publication Data

US 2021/0088573 A1 Mar. 25, 2021

(30) Foreign Application Priority Data

Sep. 25, 2019 (FR) ...................................... 1910558

(51) Int. Cl.
*G01R 31/12* (2020.01)
*G01K 1/14* (2021.01)
*G01N 33/00* (2006.01)

(52) U.S. Cl.
CPC ........... *G01R 31/1272* (2013.01); *G01K 1/14* (2013.01); *G01N 33/0031* (2013.01)

(58) Field of Classification Search
CPC ................ G01R 31/1272; G01R 31/12; G01R 31/1236; G01R 31/1245; G01R 31/1281; G01K 1/14; G01K 1/143; G01K 1/20; G01K 1/26; G01N 33/0031; G01N 33/0004; G01N 33/0009; G01N 33/0011; G01N 33/0016; G01N 33/0036; G01N 33/0039; G01N 33/0063; G01N 33/0067; G01N 33/0073; G01N 33/0075; H01J 49/168; H02J 13/00034; H02J 13/00036; H05K 1/0254; H01H 1/58; H02H 7/20; Y04S 10/30; G05B 2219/40412; G05B 23/00;
(Continued)

(56) References Cited

U.S. PATENT DOCUMENTS

| 5,107,447 A | 4/1992 | Ozawa et al. |
| 2009/0119035 A1 | 5/2009 | Younsi et al. |
| 2016/0356852 A1 | 12/2016 | Lee |

(Continued)

FOREIGN PATENT DOCUMENTS

| CN | 105606666 | 5/2016 | |
| CN | 107370036 A | * 11/2017 | ............... H02B 1/32 |

(Continued)

OTHER PUBLICATIONS

Search Report and Written Opinion for French Patent Application No. FR1910558 dated Jun. 10, 2020, 10 pages.

(Continued)

*Primary Examiner* — Daniel R Miller
*Assistant Examiner* — Eric Sebastian Von Wald
(74) *Attorney, Agent, or Firm* — Locke Lord LLP

(57) ABSTRACT

Method for monitoring for partial discharges in an electrical installation comprising at least one electrical cubicle, the electrical cubicle comprising at least one item of medium-voltage or high-voltage electrical equipment.

9 Claims, 2 Drawing Sheets

(58) Field of Classification Search
CPC ............ G05B 23/0205; G05B 23/0218; G05B 23/0221; G05D 23/2035; G05D 23/2033
See application file for complete search history.

(56) References Cited

U.S. PATENT DOCUMENTS

2019/0056446 A1* 2/2019 Dukarm ................. G01R 31/62
2021/0341520 A1* 11/2021 Davis .................... G01R 22/068

FOREIGN PATENT DOCUMENTS

| CN | 207541478 U | * | 6/2018 | ........... G05B 19/058 |
|---|---|---|---|---|
| EP | 1593981 | | 11/2005 | |
| EP | 3258278 | | 12/2017 | |
| JP | H08194878 A | * | 7/1996 | |

OTHER PUBLICATIONS

English Language Machine Translation of Chinese Patent Application Publication No. CN105606666, published on May 25, 2016, 17 pages.

Odic, E., et al., "Characterization of Medium Voltage Equipment Ageing by Monitoring of Partial Discharges Chemical and Acoustical Emission", author manuscript published in 10th International Electrical Insulation Conference, INSUCON 2006, Birmingham, UK, 2006, 6 pages.

* cited by examiner

SYSTEM FOR MONITORING FOR PARTIAL DISCHARGES IN AN ITEM OF ELECTRICAL EQUIPMENT VIA GASEOUS EMISSIONS

TECHNICAL FIELD

The present invention relates to a system and a method for monitoring for partial discharges in at least one item of medium-voltage or high-voltage electrical equipment.

The invention also relates to an electrical installation including such a monitoring system.

PRIOR ART

Medium- and high-voltage electrical equipment is constantly subjected to high current and voltage levels, and may experience partial discharges.

In the following, the terms "medium voltage" and "high voltage" are used as commonly accepted, namely with "medium voltage" referring to a voltage that is higher than 1 000 volts AC and 1 500 volts DC, but not higher than 52 000 volts AC and 75 000 volts DC, while the term "high voltage" refers to a voltage that is strictly higher than 52 000 volts AC and 75 000 volts DC.

A partial discharge is a localized electrical discharge which partially shorts an insulating material separating conductive materials, under the effect of a high voltage.

Partial discharges may in particular be caused by a manufacturing defect, uncontrolled environmental conditions or material wear.

By way of example, partial discharges in a dielectric material may occur in a gas bubble: since the permittivity of the gas is much lower than that of the surrounding material, an electric field that is significantly higher than that present within the insulating material arises. If the voltage exceeds the dielectric strength limit for the gas contained in the bubble, a partial discharge occurs. Conversely, the presence of a conductive particle in the insulator may also lead to a partial discharge.

Other types of partial discharges may occur at the surface of the insulating material or in the surrounding gases through corona discharge.

There are thus two types of partial discharge: internal partial discharges, which occur inside an insulating material, and external partial discharges, which occur on the surface or in the gases immediately surrounding the insulating material.

These partial discharges may increase the rate of deterioration of the dielectric strength of the insulating material, for example by promoting erosion or oxidation of the material. In the medium and/or long term, such deterioration may become significant and ultimately lead to breakdown across the terminals of the insulating material and to the destruction of the electrical equipment.

This results in an increased risk to the safety of the electrical equipment and hence to persons working nearby.

To limit this risk, various methods for monitoring for partial discharges in an item of electrical equipment are known, for example electrical, acoustic or optical methods.

Document EP 3 258 278 A1 thus presents a method based on an acoustic analysis correlated with measurements from temperature and humidity sensors.

Document EP 1 593 981 A2 presents a method based on an analysis of the electrical voltage and current signals when a partial discharge occurs.

Chemical methods may also be used. Specifically, external partial discharges may cause chemical reactions on the surface of the insulating materials of the electrical equipment or in the surrounding gas, in particular air. These chemical reactions result in the formation of gaseous elements, notably ozone.

The document "Characterization of medium voltage equipment ageing by monitoring of partial discharges chemical and acoustical emission, E. Odic, E. Jouseau, G. Vivien, C-S. Maroni, 10th International Electrical Insulation Conf. INSUCON 2006, Birmingham: United Kingdom (2006)" thus presents a method for monitoring for partial discharges using ozone sensors.

However, this method does not allow the specific cause of the partial discharges to be determined, but the actions to be taken to limit the occurrence of these partial discharges may depend thereon.

Additionally, such a method may prove to be inaccurate under certain conditions. Specifically, the concentration of the gaseous elements that is measured by the sensors may vary over time independently of the occurrence, or otherwise, of partial discharges, for example due to other, human activities carried out in proximity to the electrical equipment.

By way of example, it is known that some factories or motor vehicle traffic may emit ozone precursors, such as nitrogen oxide, hydrocarbons or volatile organic compounds. These ozone precursors may then react, in particular under the action of ultraviolet radiation from the sun, and form ozone.

Thus, measurements from sensors for gaseous elements may be distorted by measuring high concentrations of gaseous elements, such as ozone, independently of the occurrence, or otherwise, of partial discharges in the electrical equipment.

One of the objects of the invention is therefore to find a simple, reliable and economical system that makes it possible to detect the occurrence of partial discharges in an electrical installation, both in order to determine the cause thereof and to be sure of the effectiveness of the method used.

Additionally, the gaseous elements produced in partial discharges may have a significant effect on health, by promoting for example bronchial inflammation or scarring of lung tissue in persons working in proximity to the electrical equipment.

Another object of the invention is therefore to allow continuous and real-time monitoring so as to detect potentially dangerous partial discharges.

SUMMARY

The invention improves the situation.

What is proposed is a method for monitoring for partial discharges in an electrical installation comprising at least one electrical cubicle, the electrical cubicle comprising at least one item of medium-voltage or high-voltage electrical equipment, the electrical installation including:
- at least one first set of sensors arranged inside the electrical cubicle and at least one second set of sensors arranged outside the electrical cubicle, each of the first and second sets of sensors comprising at least one sensor for a gaseous element;
- at least one temperature sensor and/or humidity sensor arranged inside the electrical installation, the method comprising at least the following steps:

a1) comparing the concentrations of the gaseous element obtained using the first set of sensors and the second set of sensors;

a2) determining, on the basis of the comparison in step a1), whether a variation in the concentration of the gaseous element that is acquired by the first set of sensors stems from a factor external to the electrical installation;

b1) comparing the concentration of the gaseous element that is obtained by the first set of sensors with the measurements from the temperature sensor and/or humidity sensor;

b2) determining, on the basis of the comparison in step b1), whether a variation in the concentration of the gaseous element acquired by the first set of sensors stems from a variation in temperature and/or humidity inside the electrical installation; and c) if the response to steps a2) and b2) is negative, deducing that the concentration of the gaseous element that is obtained by the first set of sensors stems from a factor internal to the electrical installation.

By virtue of these arrangements, it is possible to distinguish between partial discharges caused by external factors, such as particular environmental conditions inside the electrical installation, which may promote the occurrence of one-off partial discharges, and partial discharges caused more particularly by factors internal to the electrical equipment, such as wear on the materials of the electrical equipment.

The features disclosed in the following paragraphs may, optionally, be implemented. They may be implemented independently of one another or in combination with one another:

According to one embodiment, the sensor for a gaseous element of the first and second sets of sensors is chosen from an ozone sensor, a carbon monoxide sensor, a nitric acid sensor and a nitrogen oxides sensor.

According to another embodiment, if the response to step b2) is positive, the method further comprises a step b3) of adjusting the environmental conditions inside the electrical installation.

According to another embodiment, if the response to step b2) is negative, the method further comprises a step c') of determining the state of wear of the material of the item of electrical equipment according to the concentration of the gaseous element obtained by the first set of sensors.

According to another embodiment, the method further comprises a warning step d) if the concentration of the gaseous element that is obtained by the first set of sensors is higher than a threshold value.

According to another embodiment, the internal factor is wear on the item of electrical equipment.

A "differential" or relative analysis between the sensors installed inside and outside the electrical cubicle therefore makes it possible to ensure that the electrical installation is maintained satisfactorily. Analysing absolute concentrations makes it possible to monitor the concentrations of gaseous elements and thus to protect, if necessary, the safety of persons working in proximity to the electrical installation.

According to another aspect, what is proposed is a system for monitoring for partial discharges in an electrical installation comprising at least one electrical cubicle, the electrical cubicle comprising at least one item of medium-voltage or high-voltage electrical equipment, the system including:

at least one first set of sensors arranged inside the electrical cubicle and at least one second set of sensors arranged outside the electrical cubicle, each of the first and second sets of sensors comprising at least one sensor for a gaseous element;

at least one temperature sensor and/or humidity sensor arranged inside the electrical installation, a processing unit comprising a processor configured to implement at least the following steps:

a1) comparing the concentrations of the gaseous element obtained using the first set of sensors and the second set of sensors;

a2) determining, on the basis of the comparison in step a1), whether a variation in the concentration of the gaseous element that is acquired by the first set of sensors stems from a factor external to the electrical installation;

b1) comparing the concentration of the gaseous element that is obtained by the first set of sensors with the measurements from the temperature sensor and/or humidity sensor;

b2) determining, on the basis of the comparison in step b1), whether a variation in the concentration of the gaseous element acquired by the first set of sensors stems from a variation in the temperature or in the humidity inside the electrical installation; and c) if the response to steps a2) and b2) is negative, deducing that the concentration of the gaseous element that is obtained by the first set of sensors stems from a factor internal to the electrical installation.

According to one embodiment, the system comprises a warning device.

According to another embodiment, the system comprises one or more actuators configured to adjust the environmental conditions inside the electrical installation.

BRIEF DESCRIPTION OF THE DRAWINGS

Other features, details and advantages will become apparent upon reading the description provided below and upon examining the appended drawings, in which.

DESCRIPTION OF THE EMBODIMENTS

The drawings and description below contain, for the most part, elements of certain character. They may therefore not only serve to better understand the present invention, but also contribute to the definition thereof, where appropriate.

Figure 1:
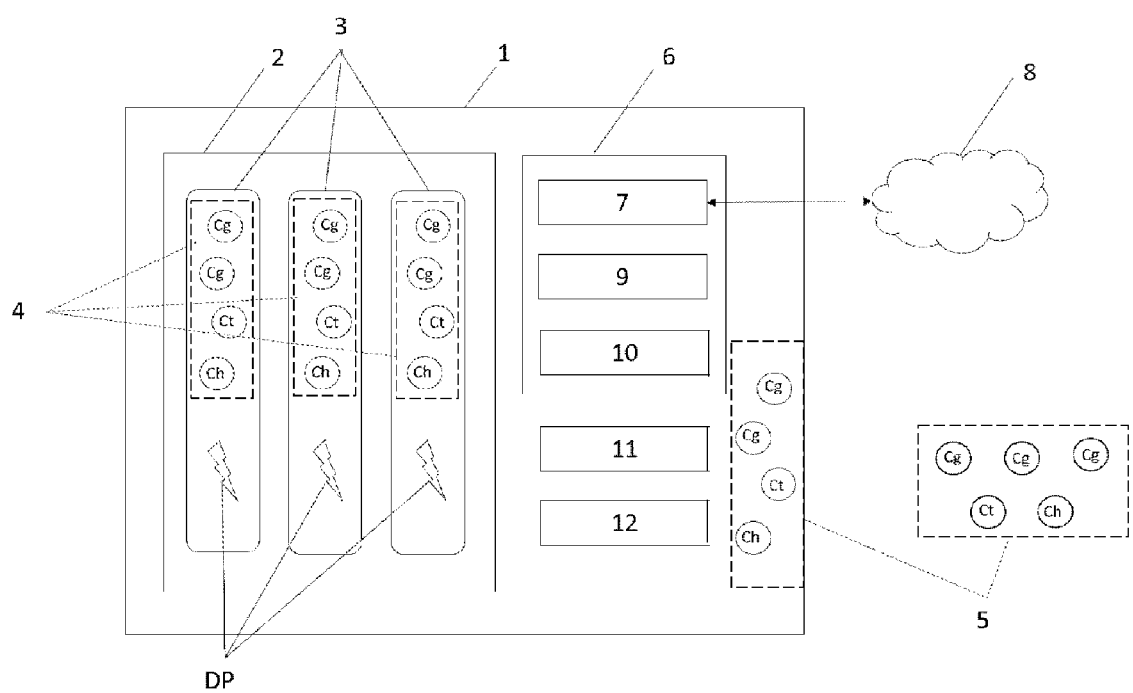
FIG. 1 is a schematic view of an installation according to one embodiment of the invention.

FIG. 1 schematically illustrates an electrical substation or installation 1 comprising one or more items of electrical equipment 3 (or electrical devices 3) arranged in an electrical cubicle 2. One or several electrical cubicles 2 can be arranged in the electrical installation 1.

According to the embodiment illustrated in FIG. 1, the electrical installation 1 comprises three items of electrical equipment 3 arranged in a single electrical cubicle 2.

The electrical installation 1 may be a station in an electrical network for the transmission and/or distribution of electricity. The electrical equipment 3 may be chosen from a switch, a circuit breaker, a contactor, a fuse switch, a recloser or a disconnector. However, other types of electrical equipment 3 are possible.

In a manner known per se, the electrical equipment 3 comprise a plurality of metal materials (such as steel, copper or aluminium) or insulating materials (such as elastomer, resin or ethylene-propylene-diene monomer). However, the use of other types of materials is of course possible, the dielectric strengths of the materials being more particularly chosen according to the target application of the electrical equipment.

The electrical installation 1 comprises a system for monitoring for partial discharges DP, in particular external partial discharges. The monitoring system comprises at least one first set of sensors 4 (called "first set" hereinafter) and a second set of sensors 5 (called "second set" hereinafter).

The first set 4 is arranged inside the electrical cubicle 2, in particular in proximity to the electrical equipment 3, while the second set 5 is arranged outside the electrical cubicle 2, in particular inside and/or outside the electrical installation 1.

According to the embodiment illustrated in FIG. 1, the first set 4 comprises sensors arranged at each of the items of electrical equipment 3 and the second set 5 comprises sensors arranged both inside and outside the electrical installation 1.

The first set 4 comprises at least one sensor for gaseous elements Cg.

The sensor for gaseous elements Cg is configured to measure a variation in or a concentration of a gaseous element. The gaseous element may be chosen from ozone ($O_3$), carbon monoxide (CO), nitric acid ($HNO_3$) and nitrogen oxides ($NO_x$). Advantageously, the gaseous element is ozone, which is one of the first gases generated in an external partial discharge. However, other gaseous elements are also conceivable.

The first set 4 also comprises at least one temperature sensor Ct and/or humidity sensor Ch. Advantageously, the first set 4 comprises both a temperature sensor Ct and humidity sensor Ch.

The first set 4 may also comprise one or more other, additional sensors configured to acquire an environmental measurement, such as a pressure, altitude or other measurement. These additional sensors may make it possible to account for climatic conditions specific to the electrical installation 1 in the analysis of the acquired measurements, according to its geographical position for example.

The sensors of the first set 4 may be arranged in the electrical cubicle 2, in particular in immediate proximity to the electrical equipment 3. The sensors of the first set 4 may for example be arranged in contact with, in particular on the outer wall of, the electrical equipment 3 or in the immediate vicinity of the electrical equipment 3 in order to measure a variation in or a concentration of a gaseous element found in the air around the electrical equipment 3.

The second set 5 comprises at least one sensor for gaseous elements Cg. In the same way as for the first set 4, the sensor for gaseous elements Cg is configured to measure a variation in or a concentration of a gaseous element. The gaseous element may be chosen from ozone ($O_3$), carbon monoxide (CO), nitric acid ($HNO_3$) and nitrogen oxides ($NO_x$). The second set 5 thus advantageously comprises the same sensors for gaseous elements as the first set 4.

The second set 5, located outside the electrical cubicle 2, makes it possible to measure variations in or the concentration of the gaseous elements over time, independently of the operation of the electrical equipment 3 and the occurrence of partial discharges.

Specifically, as pointed out above, the concentrations of some gaseous elements may vary from day to day or seasonally, for example due to human activities carried out in the environment close to the electrical installation 1. The second set 5 allows these variations to be taken into account.

In the same way as for the first set 4, the second set 5 may also comprise at least one temperature sensor Ct and/or humidity sensor Ch. Advantageously, the second set 5 comprises both a temperature sensor Ct and humidity sensor Ch.

The system also comprises a processing unit 6. The processing unit 6 is configured to analyse and process the measurements once they have been acquired by the various sensors of the first and second sets 4, 5.

The processing unit 6 thus comprises a communication interface 7 configured to receive the measurements acquired by the sensors. The communication between the processing unit 6 and the sensors may be wired or wireless, in particular via short-range protocols such as Bluetooth, Sigfox, LoRa, etc.

The communication interface 7 also makes it possible to transmit/receive information from a remote server 8. The remote server 8 may thus be configured to analyse and process the measurements acquired by the sensors remotely in combination with or as an alternative to the processing unit 6. The communication between the processing unit 6 and the remote server 8 may be wired or wireless, in particular via long-range protocols such as Ethernet or 3G/4G/5G.

The processing unit 6 also comprises a processor 9 configured to analyse, advantageously in real time, the measurements acquired by the sensors. The processor 9 may use mathematical or algorithmic tools, in particular by using an artificial intelligence.

By real time, it is understood that the method according to the invention is implemented during the operation of the electrical installation 1, within fixed time limits.

The processing unit 6 further comprises a memory 10 configured to store the measurements acquired over time by the sensors.

The system also comprises one or more warning devices 11, in particular using sound, light, messaging, etc., configured to warn persons working for the electrical installation 1, in particular in the event of high concentrations of gaseous elements as will be described below.

The system also comprises one or more actuators 12. An actuator 12 is configured to control and/or adjust the environmental conditions inside the electrical installation 1, and more particularly inside the electrical cubicle 2. An actuator 12 may for example control a heating, cooling, humidifying or dehumidifying device inside the electrical installation 1.

The method for monitoring for partial discharges inside the electrical installation 1 according to the invention is described below, in conjunction with FIG. 2.

In a step 100, the system checks the integrity and correct operation of the electrical installation 1, and in particular of the monitoring system. In particular, in a step 101, the system checks the correct operation of the first and second sets 4, 5.

If a sensor is not working or has a problem communicating with the processing unit 6, the system sends a warning message in a step 102 via the warning device 11.

If no problem is detected, the system moves on to a step 103 of acquiring measurements from the sensors. These measurements may be stored in the memory 10 of the processing system 6 and/or on the remote server 8 (step 104).

In a step 105, the system compares the measurements acquired between the first set 4 and the second set of sensors 5.

As mentioned above, some gaseous elements, such as ozone, may be produced by partial discharges but also by other factors external to and independent of the electrical installation 1. It is therefore necessary to compare the concentrations of gaseous elements obtained by the first set 4, located in the electrical cubicle 2, with the concentrations of gaseous elements obtained by the second set 5, located outside the electrical cubicle 2. This comparison may be performed by the processor 9 of the processing unit 6 and/or remotely on the remote server 8 (steps 105 and 106).

By "external factor", what is understood is a partial or total cause of the concentration of gaseous elements, generated by the occurrence of partial discharges or otherwise, which is not related to the state or operation of the electrical equipment 3. An external factor is therefore for example environmental and climatic conditions affecting the interior of the electrical installation 1 or gaseous elements emitted by elements independent of the electrical installation 1.

In contrast to an external factor, an "internal factor" is understood as a partial or total cause of the concentration of gaseous elements which is related to the state or operation of the electrical equipment 3. An internal factor is for example wear on or a manufacturing defect in the electrical equipment 3.

If the comparison indicates a difference smaller than a given threshold value, and/or a correlation in terms of concentration and timing between the measurements acquired by the first and second sets 4, 5, then it is possible to conclude that the concentrations of gaseous elements measured are due to factors external to the electrical installations 1. They are therefore not related to partial discharges that have occurred within the electrical cubicle 2.

If the comparison indicates a difference larger than a given threshold value, and/or a lack of correlation in terms of concentration and timing between the measurements acquired by the first and second sets 4, 5, then it is possible to conclude that the concentrations of gaseous elements are due to partial discharges that have occurred within the electrical cubicle 2.

The system then sends a warning message in a step 107 via the warning device 11.

These partial discharges may in particular be caused by an internal factor, in particular wear on the insulating materials of the electrical equipment 3.

According to one embodiment (not illustrated), the system may measure the deterioration, in particular by oxidation, of the materials of the electrical equipment 3 according to the concentrations of gaseous elements acquired by the sensors. It is thus possible to estimate the deterioration of the electrical equipment 3 by taking known models of the wearing and ageing of the materials into account.

In particular, the order of appearance and relative concentrations of the various gaseous elements make it possible to determine the kinetics of the chemical reactions following a partial discharge, and to refine the estimate of the deterioration of the material of the electrical equipment 3 under consideration.

However, these partial discharges may also be promoted by external factors, such as certain particular environmental conditions inside the electrical installation 1, in particular concerning the temperature and humidity inside the electrical cubicle 2. In particular, the amplitude or frequency of partial discharges may increase or decrease if the temperature and/or humidity varies.

If the sensors show a correlation between the environmental conditions (in particular temperature or humidity) inside the electrical installation 1 and the concentrations of gaseous elements (step 108), it is possible to conclude that the partial discharges are due to environmental conditions inside the electrical installation 1. The system sends a warning message in a step 109 via the warning device 11.

By way of example, the concentrations of gaseous elements may be compared with known threshold concentrations of these same gaseous elements which are normally observed for a given temperature or humidity inside the electrical installation 1.

If the sensors show an insufficient correlation, it is possible to conclude that the partial discharges are instead due to an internal factor, such as wear on the materials of the electrical equipment 3. It is therefore necessary to perform maintenance on the electrical equipment in order to ensure the safety and correct operation of the installation.

Additionally, in a step 111, the system assesses whether the concentrations of gaseous elements inside the electrical installation 1 might have a negative impact on the health of persons working inside the electrical installation 1. In the event of concentrations higher than given threshold values, the system then sends a warning message in a step 112 via the warning device 11.

According to the embodiment illustrated in FIG. 1 in which the electrical installation 1 comprises actuators 12, the system may allow, in a step 113, the environmental conditions inside the electrical installation 1 to be controlled and/or adjusted in order to limit the risks related to partial discharges. The system is thus capable of adjusting the temperature and humidity in the electrical installation 1 in order to decrease the occurrence of partial discharges, and hence the generation of gaseous elements.

The method may be implemented by means of the sensors of the first set 4 arranged in proximity to each of the items of electrical equipment 3. The arrangement of these sensors thus makes it possible to locate more precisely which item of electrical equipment 3 or electrical cubicle 2 more particularly needs to be monitored.

The method according to the invention makes it possible to improve the detection of partial discharges, to determine the causes thereof (in particular wear on the materials or environmental conditions inside the electrical cubicle), and then to perform actions inside the electrical installation 1 in order to limit the occurrence of new partial discharges or to warn the relevant persons by means of various alarm levels.

Figure 2:
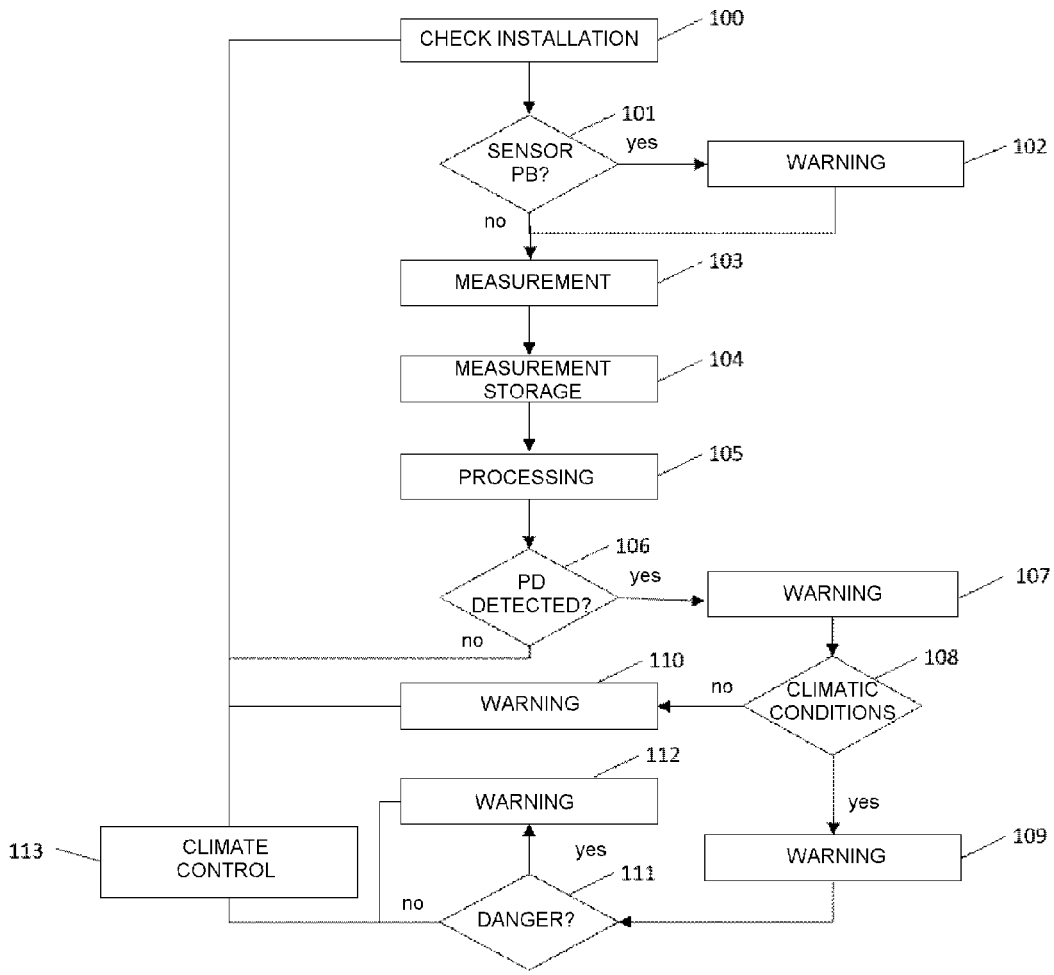
FIG. 2 is a schematic view of a monitoring method according to one embodiment of the invention.

According to the embodiment illustrated in FIG. 2, the method may then be repeated by going back through all or some of steps 100 to 113 described above. The method is thus implemented continuously.

By "continuously", it is understood that the method is implemented repeatedly advantageously for the entire duration of operation of the electrical installation 1.

Of course, the invention is not limited to the embodiments described above, which have been provided only by way of example. It encompasses various modifications, alternative forms and other variants that those skilled in the art will be able to envisage, in the context of the present invention, and in particular any combination of the various embodiments described above, which may be taken separately or in combination.

The invention claimed is:

1. Method for monitoring for partial discharges in an electrical installation comprising at least one electrical cubicle, the electrical cubicle comprising at least one item of medium-voltage or high-voltage electrical equipment, the electrical installation including:
   at least one first set of sensors arranged inside the electrical cubicle and at least one second set of sensors arranged outside the electrical cubicle, each of the first and a second sets of sensors comprising at least one sensor for a gaseous element;

at least one temperature sensor and/or humidity sensor arranged inside the electrical installation, the method comprising at least the following steps:
- a1) comparing concentrations of the gaseous element that are obtained using the first set of sensors and the second set of sensors;
- a2) determining, on the basis of the comparison in step a1), whether a variation in the concentration of the gaseous element that is acquired by the first set of sensors stems from a factor external to the electrical installation;
- b1) comparing the concentration of the gaseous element that is obtained by the first set of sensors with measurements from the temperature sensor and/or humidity sensor;
- b2) determining, on the basis of the comparison in step b1), whether a variation in the concentration of the gaseous element acquired by the first set of sensors stems from a variation in temperature and/or humidity inside the electrical installation; and
- c) determining that the responses to steps a2) and b2) are negative and deducing that the concentration of the gaseous element that is obtained by the first set of sensors stems from a factor internal to the electrical installation.

2. Method according to claim 1, wherein the sensor for a gaseous element of the first and second sets of sensors is chosen from an ozone sensor, a carbon monoxide sensor, a nitric acid sensor and a nitrogen oxides sensor.

3. Method according to claim 1, wherein when the response to step b2) is positive, the method further comprises a step b3) of adjusting the environmental conditions inside the electrical installation.

4. Method according to claim 1, wherein when the response to step b2) is negative, the method further comprises a step c') of determining the state of wear of the material of the item of electrical equipment according to the concentration of the gaseous element obtained by the first set of sensors.

5. Method according to claim 1, further comprising a warning step d) when the concentration of the gaseous element that is obtained by the first set of sensors is higher than a threshold value.

6. Method according to claim 1, wherein the internal factor is wear on the item of electrical equipment.

7. System for monitoring for partial discharges in an electrical installation comprising at least one electrical cubicle, the electrical cubicle comprising at least one item of medium-voltage or high-voltage electrical equipment, the system including:
- at least one first set of sensors arranged inside the electrical cubicle and at least one second set of sensors arranged outside the electrical cubicle, each of the first and second sets of sensors comprising at least one sensor for a gaseous element,
- at least one temperature sensor and/or humidity sensor arranged inside the electrical installation,
- a processing unit comprising a processor configured to implement at least the following steps:
  - a1) comparing concentrations of the gaseous element obtained using the first set of sensors and the second set of sensors;
  - a2) determining, on the basis of the comparison in step a1), whether a variation in the concentration of the gaseous element that is acquired by the first set of sensors stems from a factor external to the electrical installation;
  - b1) comparing the concentration of the gaseous element that is obtained by the first set of sensors with measurements from the temperature sensor and/or humidity sensor;
  - b2) determining, on the basis of the comparison in step b1), whether a variation in the concentration of the gaseous element acquired by the first set of sensors stems from a variation in the temperature or in the humidity inside the electrical installation; and
  - c) when a response responses to steps a2) and b2) is are negative, deducing that the concentration of the gaseous element that is obtained by the first set of sensors stems from a factor internal to the electrical installation.

8. System according to claim 7, comprising a warning device.

9. System according to claim 7, comprising one or more actuators configured to adjust the environmental conditions inside the electrical installation.

* * * * *